United States Patent
Kane et al.

(10) Patent No.: US 8,180,458 B2
(45) Date of Patent: May 15, 2012

(54) METHOD AND APPARATUS FOR DIGITAL SIGNAL PROCESSING FOR RADIO FREQUENCY SURGERY MEASUREMENTS

(75) Inventors: Mark L. Kane, San Jose, CA (US); Richard Wyeth, Discovery Bay, CA (US)

(73) Assignee: Thermage, Inc., Hayward, CA (US)

( * ) Notice: Subject to any disclaimer, the term of this patent is extended or adjusted under 35 U.S.C. 154(b) by 1181 days.

(21) Appl. No.: 11/958,075

(22) Filed: Dec. 17, 2007

(65) Prior Publication Data
US 2009/0157067 A1 Jun. 18, 2009

(51) Int. Cl.
*A61F 2/00* (2006.01)

(52) U.S. Cl. ............ 607/101; 607/98; 607/99; 607/115; 606/29; 606/32; 606/34; 600/547; 128/898

(58) Field of Classification Search ............ 607/96–102, 607/115–118; 606/27–52; 600/547; 128/898
See application file for complete search history.

(56) References Cited

U.S. PATENT DOCUMENTS

| | | | | |
|---|---|---|---|---|
| 3,875,945 A | * | 4/1975 | Friedman | 606/45 |
| 5,003,991 A | * | 4/1991 | Takayama et al. | 607/99 |
| 5,755,753 A | | 5/1998 | Knowlton | |
| 5,871,524 A | | 2/1999 | Knowlton | |
| 5,919,219 A | | 7/1999 | Knowlton | |
| 5,948,011 A | | 9/1999 | Knowlton | |
| 6,241,753 B1 | | 6/2001 | Knowlton | |
| 6,311,090 B1 | | 10/2001 | Knowlton | |
| 6,350,276 B1 | * | 2/2002 | Knowlton | 607/104 |
| 6,377,854 B1 | | 4/2002 | Knowlton | |
| 6,377,855 B1 | | 4/2002 | Knowlton | |
| 6,381,497 B1 | | 4/2002 | Knowlton | |
| 6,381,498 B1 | | 4/2002 | Knowlton | |
| 6,387,380 B1 | | 5/2002 | Knowlton | |
| 6,405,090 B1 | | 6/2002 | Knowlton | |
| 6,413,255 B1 | | 7/2002 | Stern | |
| 6,425,912 B1 | | 7/2002 | Knowlton | |
| 6,430,446 B1 | | 8/2002 | Knowlton | |
| 6,438,424 B1 | | 8/2002 | Knowlton | |
| 6,453,202 B1 | | 9/2002 | Knowlton | |
| 6,461,378 B1 | | 10/2002 | Knowlton | |
| 6,470,216 B1 | | 10/2002 | Knowlton | |
| 7,006,874 B2 | | 2/2006 | Knowlton et al. | |

(Continued)

FOREIGN PATENT DOCUMENTS

WO 9916502 4/1999

(Continued)

*Primary Examiner* — Linda Dvorak
*Assistant Examiner* — Adam Avigan
(74) *Attorney, Agent, or Firm* — Wood, Herron & Evans, LLP

(57) ABSTRACT

A method and apparatus for calculating current lost through a patient during a treatment of a patient using an electromagnetic energy delivery system is disclosed. The system generates electromagnetic energy, contacts a skin surface of the patient, transfers the electromagnetic energy to tissue beneath the surface of the skin, detects a value of at least one characteristic of the electromagnetic energy utilizing synchronous undersampling, and calculates the current lost through the patient. The characteristic measured may be a value of current of the electromagnet energy. An adjustable matching network may be utilized to maximize power to the tissue of the patient. Values of the impedance of the matching network may be utilized to determine the electromagnetic energy delivered to the tissue of the patient. A current correction factor is determined from the impedance of the matching network and utilized to calculate the current lost through the patient.

16 Claims, 2 Drawing Sheets

U.S. PATENT DOCUMENTS

| | | | |
|---|---|---|---|
| 7,022,121 B2 | 4/2006 | Stern et al. | |
| 7,115,123 B2 | 10/2006 | Knowlton et al. | |
| 7,141,049 B2 | 11/2006 | Stern et al. | |
| 7,189,230 B2 | 3/2007 | Knowlton | |
| D544,955 S | 6/2007 | Carson et al. | |
| 7,229,436 B2 | 6/2007 | Stern et al. | |
| 7,257,450 B2 | 8/2007 | Auth et al. | |
| 7,267,675 B2 | 9/2007 | Stern et al. | |
| 7,452,358 B2 | 11/2008 | Stern et al. | |
| 7,473,251 B2 | 1/2009 | Knowlton et al. | |
| 7,473,252 B2 | 1/2009 | Barry | |
| 7,477,711 B2 * | 1/2009 | Kalvaitis et al. | 375/355 |
| 7,481,809 B2 | 1/2009 | Stern et al. | |
| 7,494,488 B2 | 2/2009 | Weber | |
| 2006/0262889 A1 | 11/2006 | Kalvaitis et al. | |

FOREIGN PATENT DOCUMENTS

| | | |
|---|---|---|
| WO | 0053113 | 9/2000 |
| WO | 0100269 | 1/2001 |
| WO | 03053266 | 3/2003 |
| WO | 03065915 | 8/2003 |
| WO | 03065916 | 8/2003 |
| WO | 03086217 | 10/2003 |
| WO | 2004086943 | 10/2004 |
| WO | 2004087253 | 10/2004 |
| WO | 2004088700 | 10/2004 |
| WO | 2004089185 | 10/2004 |
| WO | 2004089186 | 10/2004 |
| WO | 2004089459 | 10/2004 |
| WO | 2004089460 | 10/2004 |
| WO | 2004090939 | 10/2004 |
| WO | 2004105861 | 12/2004 |

* cited by examiner

METHOD AND APPARATUS FOR DIGITAL SIGNAL PROCESSING FOR RADIO FREQUENCY SURGERY MEASUREMENTS

FIELD OF THE INVENTION

The present invention relates generally to a treatment device, and more particularly to digital signal processing of radio frequency signals of the treatment device.

BACKGROUND OF THE INVENTION

Soft tissue remodeling is a biophysical phenomenon that occurs at cellular and molecular levels. Molecular contraction or partial denaturization of collagen involves the application of an energy source, which destabilizes the longitudinal axis of the molecule by cleaving heat labile bonds of a triple helix. As a result, stress is created to break the intermolecular bonds of the matrix. This is essentially an immediate extra-cellular process, whereas cellular contraction requires a lag period for the migration and multiplication of fibroblasts into a wound as provided by a wound healing sequence. In higher developed animal species, the wound healing response to an injury involves an initial inflammatory process that subsequently leads to the deposition of scar tissue.

The initial inflammatory response consists of the infiltration by white blood cells or leukocytes that dispose of cellular debris. Approximately seventy-two hours later, proliferation of fibroblasts occurs at the injured site. These cells differentiate into contractile myofibroblasts, which are the source of cellular soft tissue contraction. Following cellular soft tissue contraction, collagen is laid down as a static scar supporting matrix in the tightened soft tissue structure. The deposition and subsequent remodeling of this nascent scar matrix provides the means to alter the consistency and geometry of soft tissue for aesthetic purposes.

In light of the preceding discussion, there are a number of dermatological procedures that lend themselves to treatments which deliver thermal energy to skin and underlying tissue to cause a contraction of collagen and/or initiate a wound healing response. Such procedures include skin remodeling/resurfacing, wrinkle removal, and treatment of the sebaceous glands, hair follicles, adipose tissue, and spider veins.

Currently available technologies that deliver thermal energy to the skin and underlying tissue include electromagnetic energy, optical (laser), ultrasound and direct heating with a hot surface. In particular, electromagnetic energy may take the form of Radio Frequency (RF) energy.

RF based surgery demands knowledge of the electrical properties of the applied RF. These properties include accurate values of power, energy, and current delivered to a patient. For example, to receive the desired cosmetic effects using an RF energy delivery system a precise accumulated dose of RF energy must be delivered to the patient. Contemporary treatment protocols require accurate control of either RF current or RF power until a prescribed quantity of energy is accumulated or an appropriate time-out period has elapsed. Because of the differences from one patient to another, tissue resistance and RF current passing through the patient are highly variable. Consequently, to maximize the power to the patient it follows that a matching impedance of the electromagnetic energy source used in the RF surgery must be adaptable. Knowledge of the properties of the applied RF, patient tissue resistance, patient RF current and matching impedance are required to choose a current that will result in reaching a prescribed energy level within a specified treatment time period.

The high frequency RF signals of an electromagnetic energy delivery system, which may be in the Megahertz range, are delivered to the patient over electrical cables that are generally two meters long. The electromagnetic energy delivery system typically comprises an electromagnetic energy delivery device (typically a handpiece) to transmit the electromagnetic energy, and an electromagnetic energy source (generator) to produce the RF signals. RF energy is coupled into the patient capacitively through a tip in the handpiece.

A challenge with transferring the RF energy capacitively is that the patient has stray capacitance to earth ground that provides a bypass path for the RF current, leading to skewed measurements of the RF current or RF power. For example, taking measurements of the RF current or RF power at the generator (which may be remote from the patient) is challenging because cable impedances, insert capacitance, patient stray bypass capacitance, and the resultant effects on the measurement data value are all variable. However, the RF current and RF power must be known to calculate the total RF energy transmitted to the patient. Too much RF energy may result in burns, while too little RF energy may not provide the desired result.

To optimize the transfer of RF energy and maintain high electrical efficiency in the generator, the adaptable matching network may be utilized. The matching network compensates for capacitive and inductive reactance in the RF cables, insert capacitance, variable stray capacitance to earth ground, and variable tissue resistance. The matching network operates to maximize the RF energy transferred to the patient.

Tunable reactive components in the matching network may be adjusted to achieve an acceptable impedance match between the RF generator output stage and the compensated RF load impedance. The matching network is adjusted prior to a surgical RF delivery such that the RF current and voltage are approximately in phase and a directional coupler indicates a minimum in the reflected power coefficient, or ratio of reflected power to forward power.

Current sense transformers located at the RF output and return sense current delivered to the patient. However, a variable current that bypasses the patient through stray capacitance may be difficult to remotely determine. The bypass current may be needed to accurately calculate the amount of RF energy that has actually been transferred to the patient.

Calculating root mean square (RMS) values of the RF current and RF power at frequencies in the MHz range can also be challenging. Measuring the RMS RF current or RMS RF power at high frequencies is difficult due to the state of contemporary sensor devices. One way to measure RMS RF current and voltage is through an active peak detector. The RMS value is then calculated using the standard formula of 0.707 times the peak value. However, the active peak detector only detects and measures the high and low peaks of an RF signal without any consideration of possible harmonics. Additionally, the active peak detector is limited to applications where there is a pure sinusoidal waveform. Furthermore, the operating frequency for an active peak detection circuit requires that it detect peaks at many times the operating frequency of the signal it is measuring. Due to limitations in contemporary technology, this method is challenging and results in less accurate readings.

Another way to measure the peak value of the RF current and voltage at high frequencies is to utilize a diode circuit. However, diode circuits generally produce nonlinearities and harmonics or otherwise introduce inaccuracies into the measurements. At the operating frequencies of an electromagnetic energy delivery system, these inaccuracies make diode circuits a less than attractive alternative.

As shown in detail above, measuring the outputs of an RF surgical device presents numerous challenges. Consequently, there is need for an improved method and apparatus for performing critical RF signal measurements of an RF energy delivery system.

SUMMARY OF THE INVENTION

Embodiments of the invention provide a method and apparatus utilizing undersampling techniques that address the challenges of performing critical RF signal measurements. Embodiments of the invention provide a method of measuring the electromagnetic energy generated from an electromagnetic energy delivery system that includes a processor and a memory. A skin contacting portion of the electromagnetic energy delivery system contacts a patient's skin surface and transfers electromagnetic energy to a tissue beneath the skin surface of the patient. The electromagnetic energy delivery system detects a value of at least one characteristic of the electromagnetic energy by way of synchronous undersampling. In some embodiments, the characteristic detected is a current value of the electromagnetic energy. The current lost through the patient is calculated to determine the actual energy delivered to a patient.

In some embodiments, a matching network having an adjustable impedance is established. A current correction factor is calculated from the resistive value of the impedance of the matching network and the inductive value of the impedance of the matching network. In some embodiments, the current correction factor is determined from a software lookup table. In some embodiments, the current correction factor may be utilized to determine the value of current lost through the patient. In some embodiments, the value of current lost through the patient may be utilized to determine the electromagnetic energy transferred to the patient. In some embodiments, the transfer of electromagnetic energy may be substantially terminated when a predetermined amount of electromagnetic energy has been delivered.

These and other advantages will be apparent in light of the following figures and detailed description.

BRIEF DESCRIPTION OF THE DRAWINGS

The accompanying drawings, which are incorporated in and constitute a part of this specification, illustrate embodiments of the invention and, together with a general description of the invention given above and the detailed description of the embodiments given below, serve to explain the principles of the invention.

DETAILED DESCRIPTION

Figure 1:
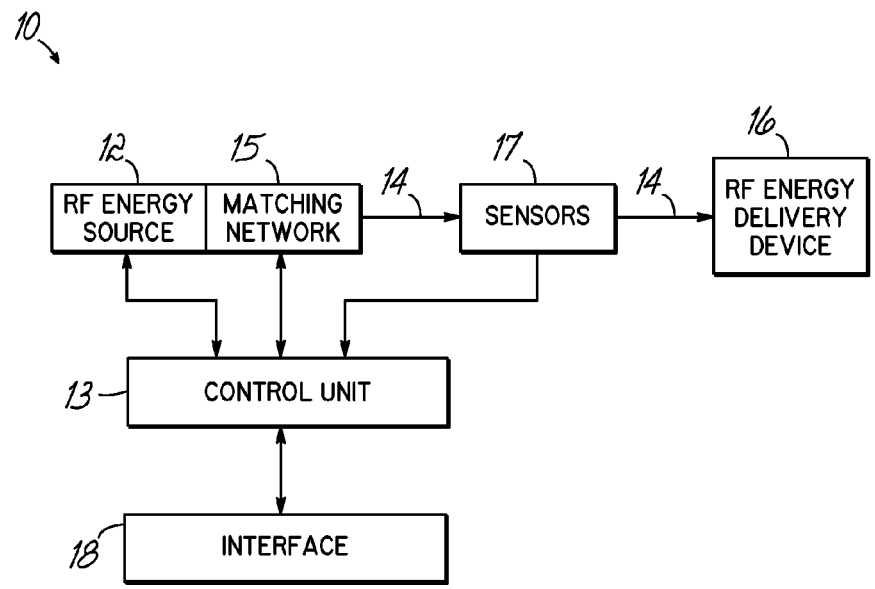
FIG. 1 is a diagrammatic illustration of an electromagnetic energy delivery system consistent with embodiments of the invention.

Turning now to the drawings, wherein like numbers denote like parts throughout the several views, FIG. 1 is a diagrammatic illustration of an electromagnetic energy delivery system 10 sufficient for use as a Radio Frequency ("RF") surgical device and consistent with embodiments of the present invention. The electromagnetic energy delivery system 10 includes an RF energy source 12 in electrical communication with a control unit 13. One end of a coaxial cable 14 is electrically connected to the RF energy source 12 through a configurable matching impedance network 15. An RF energy delivery device 16 is electrically connected to the opposing end of the coaxial cable 14. At least one sensor 17 is in electrical communication with the coaxial cable 14 and control unit 13. Sensors 17 transmit signals corresponding to phase, voltage, and current of the forward and reflected signal on the coaxial cable 14 to the control unit 13.

In one embodiment, the RF energy source 12 is a generator that includes a high-frequency oscillator operative to produce a high frequency signal in the range of approximately 200 MHz to approximately 500 MHz. A "Divide by N" (D/N) counter inside the RF energy source is configured to divide the high frequency signal by a value, N1, to produce a reference signal in the frequency range of approximately 4 MHz to approximately 8 MHz. The reference signal is operable to produce a periodic RF signal of like frequency from the RF energy source 12.

In some embodiments, RF energy delivery device 16 is a handpiece operative to couple to a patient and transfer RF energy such as that disclosed in U.S. Pat. No. 7,006,874 entitled "Treatment Apparatus with Electromagnetic Energy Delivery Device and Non-Volatile Memory," the disclosure of which is incorporated herein by reference in its entirety. The RF energy transmitted from RF energy source 12 through the coaxial cable 14 and to the RF energy delivery device 16 takes the form of the periodic RF signal. The RF energy delivery device 16 delivers RF energy to a tissue of the patient during an RF surgical procedure. In particular, the RF energy delivery device 16 contacts a skin surface of a patient with a skin contacting portion. RF energy is then transferred from the RF energy delivery device 16 to tissue beneath the surface of the skin. For accurate surgical procedures, it is necessary to know the precise amount of energy transferred to the patient. To determine the energy transferred to the patient, the control unit 13 is operable to determine RF signal characteristics synchronously and calculate precise power delivered to the patient.

Control unit 13 measures the forward and reflected characteristics of the RF signal on the coaxial cable 14. In some embodiments, control unit 13 is in electrical communication with a conducting wire and a conducting sheath of the coaxial cable 14 directly through sensors 17. In this way, control unit 13 measures the output characteristics of the RF signal with at least one sensor 17 connected to the conducting wire of the coaxial cable 14 and the reflected characteristics of the RF signal with at least one sensor 17 connected to the conducting sheath of the coaxial cable 14. Sensors 17 may be configured to provide the control unit 13 with signals corresponding to the forward power of the RF signal, the reflected power of the RF signal, the reflected voltage of the RF signal, the monopolar current of the RF signal, the bipolar current of the RF signal, and/or the reflected current of the RF signal. In alternate embodiments, control unit 13 may be coupled to the coaxial cable 14 and associated sensors 17 remotely through a network.

The control unit 13 analyzes the measured characteristics of the RF signal and determines the energy transferred to the patient during an RF surgical procedure. In this way, the control unit 13 is operable to calculate the tissue resistance and stray capacitance of the patient. In some embodiments, the control unit 13 adjusts the matching network 15 to compensate for patient tissue resistance, variable patient stray capacitance, capacitive and inductive reactance in the coaxial cable 14, and insert capacitance of the RF energy delivery system. Matching the complex resistivity of the coaxial cable 14, RF energy delivery device 16, and patient tissue with the adjustable matching network 15 may maximize power transferred to the patient during the RF surgical procedure. In some embodiments, the control unit 13 obtains values for the patient load and electromagnetic energy delivery system load though analysis of the output and reflected characteristics of the RF signal. The real component of the resistivity of the matching impedance network will correspond to the tissue resistance of the patient. The complex component of the resistivity of the matching impedance network will correspond to the stray capacitance of the patient. In alternate embodiments, the control unit 13 is connected to a directional coupler (not shown) operable to indicate the reflected power coefficient, or ratio of reflected power to forward power. The control unit 13 adjusts the matching network 15 and monitors the directional coupler for an indication that there is maximum power transferred to the patient. In this way, the control unit 13 compensates for patient tissue resistance, variable patient stray capacitance, capacitive and inductive reactance in the coaxial cable 14, and insert capacitance of the RF energy delivery system to maximize power transferred to a patient during an RF surgical procedure.

Control unit 13 may be incorporated in the same housing as RF energy source 12 and matching network 15. In alternate embodiments, control unit 13 may be incorporated into RF energy delivery device 16. Incorporating control unit 13 into the same housing as RF energy source 12 is believed to assist in reducing wear and prolong the operating life of control unit 13. The RF energy delivery device 16 may experience extreme environments resulting from continual handling, inadvertent dropping, and other jarring motion. Control unit 13 controls operation of the RF energy source 12 and may terminate the operation of the electromagnetic energy delivery system 10 if a failure has occurred. Similarly, control unit 13 may terminate operation of the RF energy source 12 or RF energy delivery device 16 if a predetermined amount of RF energy has been transferred.

Control unit 13 is in electrical communication with an interface 18 that indicates error conditions of the electromagnetic energy delivery system 10, information about RF signal characteristics of the electromagnetic energy delivery system 10, and completion of treatment of the patient. Interface 18 may also be used to input commands into the electromagnetic energy delivery system 10, such as desired energy to the patient, desired time of treatment, a command to shut-down the electromagnetic energy delivery system 10, and desired configuration of the electromagnetic energy delivery system 10.

Characteristics of the RF signal may be determined by synchronously sampling the RF signal with the control unit 13. In some embodiments, the control unit 13 measures characteristics of the RF signal at a different frequency than the frequency of the RF signal to accurately measure the characteristics of the RF signal. For example, an RF signal may be oversampled at a frequency at least twice as high as the highest frequency of the RF signal; however, oversampling an RF signal from an electromagnetic energy delivery system, such as that from FIG. 1, results in high overhead costs including multiple expensive components for peak detection and scaling. At the high operating frequencies of the electromagnetic energy delivery system 10 illustrated in FIG. 1, it may be difficult to oversample an RF signal and accurately capture signal characteristics because of the high speed requirements of circuitry components. Similarly, the high speed operating requirements to oversample an RF signal may result in the need for circuitry components that are very expensive. Additionally, at higher frequencies, such as those in the electromagnetic energy delivery system 10, it may be difficult to determine the significant higher order Fourier harmonic components of an RF signal. Therefore, the approach taken by the control unit 13, in some embodiments, is to determine the RF signal characteristics by synchronously undersampling the signal.

Figure 2:
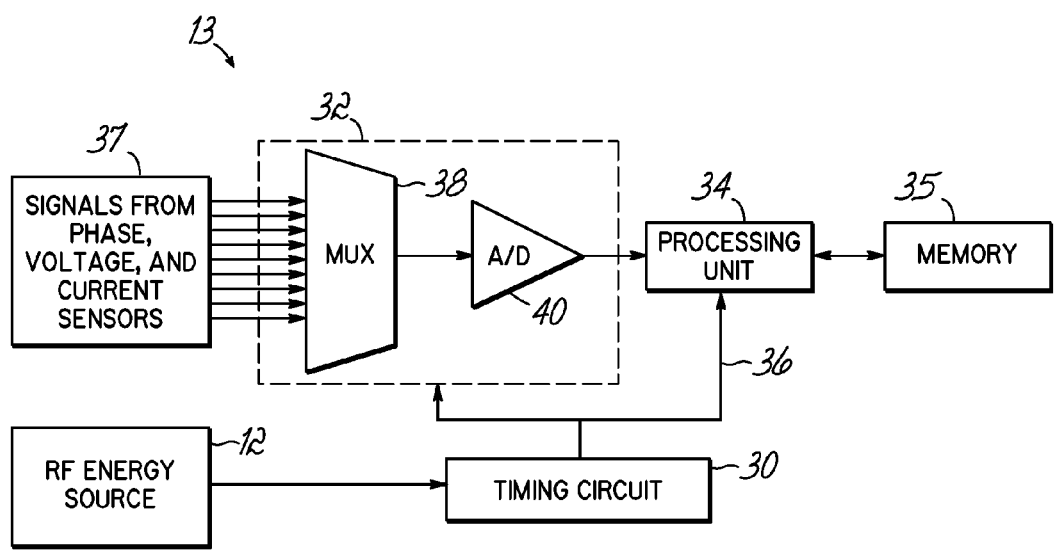
FIG. 2 is a diagrammatic illustration that provides additional detail of the control unit of the electromagnetic energy delivery system of FIG. 1.

FIG. 2 is a diagrammatic illustration of an embodiment of control unit 13 that includes a timing circuit 30, an analog-to-digital (A/D) unit 32, and a processing unit 34 utilized to undersample an RF signal. Timing circuit 30 is in electrical communication with a high frequency signal from RF energy source 12 and configured to produce a timing signal operative as a clock signal on clock signal line 36 for A/D unit 32 and processing unit 34. In the illustrated embodiment in FIG. 2, A/D unit 32 is comprised of a multiplexer (MUX) 38 and an A/D converter 40. In some embodiments, processing unit 34 may be one or more field programmable gate array ("FPGA"), one or more processors, one or more controllers, or other programmable logic devices. Processing unit 34 may also include a memory 35 operable to store signal characteristics and system configuration settings.

Timing circuit 30 may utilize a D/N counter (not shown) in a similar way as used by the RF energy source 12 described above. In one embodiment, a D/N counter in timing circuit 30 transforms the high frequency signal from RF energy source 12 into a clock signal output on clock signal line 36. The clock signal produces an operational frequency for control unit 13 to undersample the characteristics of the RF signal. In an alternate embodiment, timing circuit 30 may be incorporated into processing unit 34.

Undersampling samples a signal at frequencies that are lower than the lowest frequency of the signal. Because the RF signal is periodic, a delay between samples does not affect the accuracy of the characteristics measured. Furthermore, undersampling reduces the requirements on the upper magnitude of the operational frequency signal for the A/D unit 32 and the processing unit 34, generally resulting in lower costs of implementation. Undersampling may compensate for spikes or noise in the RF signal while retaining the ability to detect up to the tenth harmonic of the RF signal.

Figure 3:
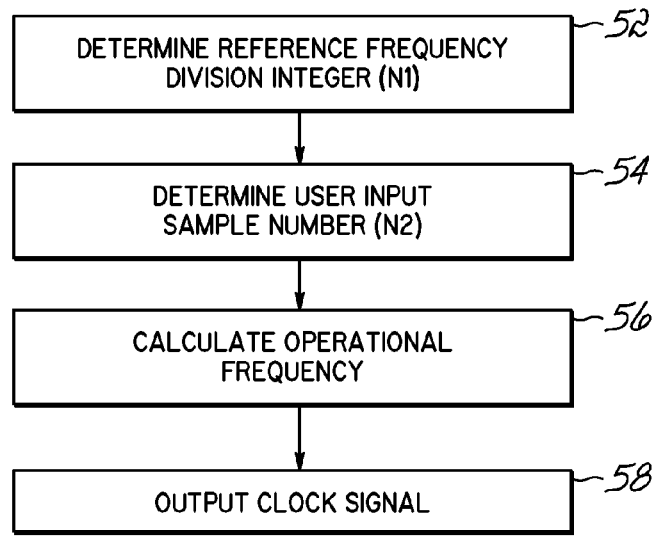
FIG. 3 is a flow chart illustrating the steps of calculating the operational frequency of the control unit shown in FIGS. 1 and 2 to undersample the characteristics of a Radio Frequency signal.

FIG. 3 illustrates a flowchart to produce a clock signal used to undersample an RF signal by a control unit such as that shown in FIGS. 1 and 2. In step 52, a value corresponding to N1 is determined by the timing circuit 30. As disclosed above, the value of N1 corresponds to a value used to divide the high frequency signal from the RF energy source 12 resulting in the frequency of the RF signal, approximately 4 MHz to 8 MHz. In one embodiment, the oscillation frequency of the high frequency oscillator in RF energy source 12 is known, allowing N1 to be a constant stored in memory 35 and retrieved by timing circuit 30.

In step 54, a user input sample number ("N2") is determined. An operator of the electromagnetic energy delivery system specifies N2 by way of a prompt at interface 18. In an alternate embodiment, the control unit 13 is programmed with a fixed N2. N2 is placed in a denominator (1/N2) and added to N1 to calculate operational frequency suitable for the control unit 13 to undersample the RF signal.

The operational frequency is calculated in step 56. The D/N counter in the timing circuit 30 calculates the operational frequency ($F_{OPERATING}$) by dividing the high frequency signal ($F_{HIGH}$) from the RF energy source 12 by the sum of N1 and 1/N2:

$$F_{OPERATING} = \frac{F_{HIGH}}{\left(N1 + \frac{1}{N2}\right)}$$

Any positive integer value of N2 results in a lower operational frequency than the frequency of the RF signal. Generally, N2 is a whole number that is always greater than a value of 2. In some embodiments, N2 has a value greater than 10 to reduce measured effects of random noise and occasional noise on the RF signal. At step 58, timing circuit 30 produces a clock signal corresponding to the operational frequency to control the operation of A/D unit 32 and processing unit 34.

Referring again to FIG. 2, A/D unit 32 receives clock signals from the timing circuit 30 and receives signals corresponding to forward and reflected power, phase, and current from the sensors 17 in the block shown generally as signal block 37. Upon receiving a pulse from clock signal line 36, A/D unit 32 converts an analog value of an RF signal characteristic from the signal block 37 into a digital value. A pulse from clock signal line 36 switches connections in MUX 38 to a particular characteristic line, allowing an analog signal characteristic to proceed to A/D converter 40. A/D converter 40 converts the analog characteristic to a digital value, which proceeds to the processing unit 34 for analysis or storage in memory 35. In this way, the control unit 13 synchronously samples and determines characteristics of the RF signal.

Processing unit 34 may be configured to store the measured characteristics and calculate an RMS value for each characteristic in memory 35. Processing unit 34 may calculate the RMS value for each characteristic ($C_{RMS}$) by computing the sum of the squares of the values of the sample points measured at $F_{OPERATING}$ ($C_{N2}$), then dividing by an appropriate constant that is related to the number of total samples in the computation and the scaling of the units of the measured parameter, then taking the square root of that final value. For example, a formula for $C_{RMS}$ may be notated as follows:

$$C_{RMS} = \sqrt{\frac{\Sigma (C_{N2})^2}{N2}}$$

The RMS values for certain characteristics are then analyzed to obtain values of tissue resistance and stray capacitance of the patient. Values of tissue resistance and stray capacitance are in turn analyzed to obtain a current correction factor to apply to the measured forward current in order to calculate a precise value of RF energy transferred to the patient.

Transfer of maximum power to the patient utilizing the electromagnetic energy delivery system 10 requires the output impedance of the RF energy source 12 to be equal to the input impedance of the coaxial cable 14, RF energy delivery device 16, and the patient. In one embodiment, after the RF energy delivery device 16 has been applied to a patient, but before the surgical procedure has been started, the control unit 13 analyzes the RMS values of reflected current and reflected voltage of the RF signal to calculate the tissue resistance of the patient. The value of tissue resistance of the patient is matched by the matching network 15 to maximize power to the patient. The control unit 13 analyzes the phase difference between the reflected current and reflected voltage of the RF signal and adjusts matching network 15 until zero phase difference is detected. This zero phase difference indicates that the capacitive value of the patient impedance has been matched by an inductive value in the matching network 15. After the matching network 15 has been adjusted to eliminate the phase difference to the patient, the control unit 13 has an accurate measurement of the total value of the matching network impedance. In particular, control unit 13 associates patient tissue resistance with the resistive value of the matching network impedance and control unit 13 associates a tuning inductance with the inductive value of the matching network impedance. In some embodiments, the matching network 15 is an array of resistive, inductive, and capacitive elements that can be varied by the control unit 13 to obtain a matching network impedance in relation to the patient load.

Figure 4:
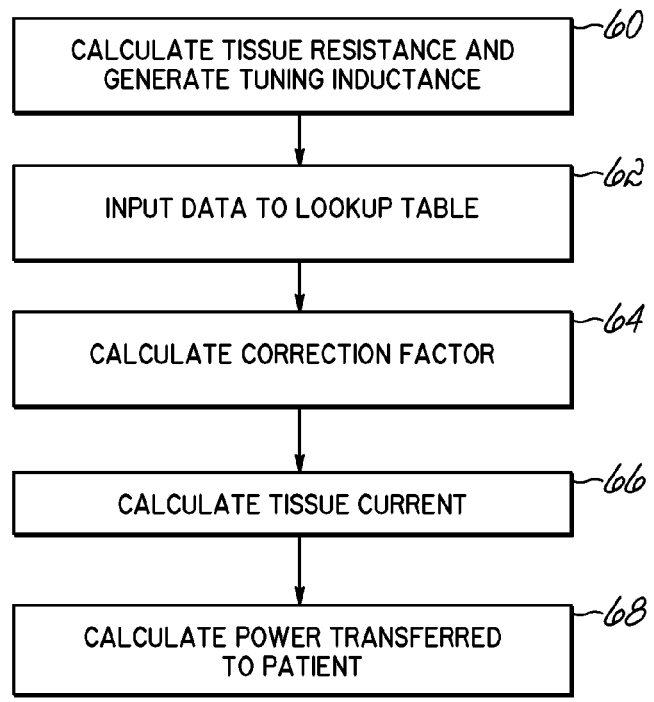
FIG. 4 is a flow chart illustrating the steps of calculating the actual current and power delivered to a patient from an electromagnetic energy delivery system of FIG. 1 and consistent with embodiments of the invention.

FIG. 4 is a flow chart view of the process to calculate a highly accurate value of power transferred to the patient during RF surgery using an electromagnetic energy delivery system 10 such as that disclosed in FIG. 1. In step 60, the tissue resistance of the patient is calculated and the tuning inductance is generated by the control unit 13. At step 62, controller unit 13 utilizes the values of tissue resistance and tuning inductance as data inputs to a software lookup table stored in memory 35. The software lookup table is configured to utilize the tissue resistance and tuning inductance as data inputs and to output a current correction factor in step 64. The control unit 13 uses the current correction factor to calculate the tissue current of the patient at step 66 by multiplying the current correction factor by the RMS value of the RF current. In an alternate embodiment, the software lookup table may be used to generate a power correction factor or tissue resistance correction factor. A current correction factor, power correction factor, or tissue resistance factor is calculated during calibration of the electromagnetic energy delivery system 10 before an RF surgical procedure. A correction factor in some embodiments may be between a value of approximately 0.67 and approximately 0.95. In another alternate embodiment, the control unit 13 may directly calculate a current correction factor from the values of tissue resistance and tuning inductance.

In step 68, control unit 13 calculates the actual power transferred to a patient during an RF surgical procedure. During an RF surgical procedure, control unit 13 monitors and calculates RMS values for the forward power, reflected power, forward monopolar current, forward bipolar current, reflected current, and reflected voltage of the RF signal utilizing undersampling. By multiplying the current correction factor by the RMS value for forward bipolar current, a value for tissue current of the patient can be calculated. Actual tissue resistance is then calculated from the values of corrected forward bipolar current and forward power. Using the values of actual tissue resistance and tissue current, a value of power transferred to a patient during an RF surgical procedure is calculated. This value of power transferred to the patient is used by control unit 13 to operate electromagnetic energy delivery system 10 for a set amount of time or total power transferred and ensure a patient is not harmed during an RF surgical procedure.

While the present invention has been illustrated by a description of the various embodiments and while these embodiments have been described in considerable detail, it is not the intention of the applicants to restrict or in any way limit the scope of the appended claims to such detail. Additional advantages and modifications will readily appear to those skilled in the art. Thus, the invention in its broader aspects is therefore not limited to the specific details, representative apparatus and method, and illustrative example shown and described. Accordingly, departures may be made from such details without departing from the spirit or scope of applicants' general inventive concept.

What is claimed is:

1. A method of measuring electromagnetic energy generated from an electromagnetic energy delivery system, the method comprising:
   contacting a skin surface of the patient with a skin contacting portion of the electromagnetic energy delivery system;
   generating electromagnetic energy, wherein the electromagnetic energy is a radio-frequency signal;
   transferring the electromagnetic energy from the electromagnetic energy delivery system to tissue beneath the skin surface of the patient through the skin contacting portion;
   measuring a value of current of the electromagnetic energy, wherein the value of the current is measured utilizing synchronous undersampling; and
   calculating a value of current lost through the patient,
   wherein calculating the value of current lost through the patient comprises calculating a current correction factor based on a value of patient tissue resistance and a value of tuning inductance.

2. The method of claim 1, wherein calculating the value of current lost through the patient further comprises:
   establishing a matching network having an adjustable impedance for the electromagnetic energy delivery system,
   wherein the matching network is configured to match an impedance of the patient, and a resistive value of the impedance of the matching network corresponds to the value of patient tissue resistance, and an inductive value of the impedance of the matching network corresponds to the value of tuning inductance of the electromagnetic energy delivery system.

3. The method of claim 2, wherein the electromagnetic energy delivery system includes a memory, and calculating the current correction factor comprises:
   referencing a software lookup table to determine the current correction factor using the value of patient tissue resistance and the value of tuning inductance, wherein the software lookup table is stored in the memory.

4. The method of claim 2, wherein calculating the value of current lost through the patient further comprises:
   calculating the current lost through the patient from the current correction factor and the measured value of current.

5. The method of claim 2, further comprising:
   determining the electromagnetic energy transferred to the patient from the value of current lost through the patient and the value of patient tissue resistance.

6. The method of claim 5, further comprising:
   substantially terminating the transfer of electromagnetic energy from the electromagnetic energy delivery system when a predetermined value of electromagnetic energy has been transferred to the tissue of the patient.

7. An apparatus for determining a value of current lost through a patient from an electromagnetic energy delivery system during a treatment of the patient, the apparatus comprising:
   an electromagnetic energy source operable to generate electromagnetic energy, wherein the electromagnetic energy is a radio-frequency signal;
   a coaxial cable electrically connected to the electromagnetic energy source;
   an electromagnetic energy delivery device having a skin contacting portion, wherein the electromagnetic energy delivery device is electrically connected to the coaxial cable and configured to contact a skin surface of the patient with the skin contacting portion, and wherein the skin contacting portion transfers the electromagnetic energy to a tissue beneath the skin surface of the patient during the treatment of the patient;
   a control unit electrically connected to the electromagnetic energy source and in electrical communication with the coaxial cable; and
   a sensor electrically connected to the coaxial cable, the sensor in electrical communication with the control unit, and the sensor configured to provide signals representing a current of the radio-frequency signal on the coaxial cable to the control unit,
   wherein the control unit is operable to measure a value of the current utilizing synchronous undersampling of the radio-frequency signal in the signals provided from the sensor, to calculate the value of current lost through the patient, and to calculate a current correction factor based on a value of patient tissue resistance and a value of tuning inductance.

8. The apparatus of claim 7, wherein the control unit further comprises:
   a processing unit; and
   a memory.

9. The apparatus of claim 8, further comprising:
   an adjustable matching network electrically connected to the coaxial cable, the adjustable matching network configured to maximize power transferred to the patient through the skin contacting portion of the electromagnetic energy delivery device.

10. The apparatus of claim 9, wherein the control unit is further operable to adjust the adjustable matching network.

11. The apparatus of claim 7, wherein a resistive value of the impedance of the matching network corresponds to the value of patient tissue resistance, and an inductive value of the impedance of the matching network corresponds to the value of tuning inductance of the electromagnetic energy delivery system.

12. The apparatus of claim 11, wherein the control unit is further operable to reference a software lookup table in memory to determine the current correction factor using the value of the tissue resistance of the patient and the value of the tuning inductance.

13. The apparatus of claim 11, wherein the control unit is further operable to determine the value of current lost through the patient from the current correction factor and the value of current transmitted by the sensor.

14. The apparatus of claim 11, wherein the control unit is further operable to determine the electromagnetic energy transferred to the patient from the value of current lost through the patient and the value of patient tissue resistance.

15. The apparatus of claim 14, wherein the control unit is further operable to substantially terminate the transfer of electromagnetic energy from the electromagnetic energy delivery system when a predetermined value of electromagnetic energy has been transferred to the tissue of the patient.

16. The apparatus of claim 7, further comprising:
   an interface in electrical communication with the control unit.

* * * * *